United States Patent [19]
Yanobu

[11] Patent Number: 5,852,267
[45] Date of Patent: Dec. 22, 1998

[54] INJECTION NEEDLE SAFETY DISPOSAL APPARATUS

[75] Inventor: Toshio Yanobu, Kyoto, Japan

[73] Assignees: Taiyo Elecs Co., LTD., Kyoto; OKI Customer Advanced-Technology Co., LTD., Tokyo, both of Japan

[21] Appl. No.: 720,505

[22] Filed: Sep. 30, 1996

Related U.S. Application Data

[63] Continuation-in-part of Ser. No. 565,427, Nov. 30, 1995, Pat. No. 5,676,859.

[30] Foreign Application Priority Data

Jun. 26, 1996 [JP] Japan .................................... 8-165527

[51] Int. Cl.$^6$ ........................... B23K 11/22; A61G 12/00; A61L 11/00
[52] U.S. Cl. .............................................................. 219/68
[58] Field of Search ................................................. 219/68

[56] References Cited

U.S. PATENT DOCUMENTS

| | | | |
|---|---|---|---|
| 4,877,934 | 10/1989 | Spinello | 219/68 |
| 5,212,362 | 5/1993 | Burden et al. | 219/68 |
| 5,264,675 | 11/1993 | Butler | 219/68 |
| 5,282,428 | 2/1994 | Greville et al. | 219/68 |
| 5,336,862 | 8/1994 | Yelvington | 219/68 |
| 5,365,029 | 11/1994 | Makihara | 219/68 |
| 5,548,095 | 8/1996 | Cornell | 219/68 |
| 5,551,355 | 9/1996 | Haines et al. | 219/68 |
| 5,676,859 | 10/1997 | Yanobu | 219/68 |

FOREIGN PATENT DOCUMENTS

| | | |
|---|---|---|
| 1-320057 | 12/1989 | Japan . |
| 4-126146 | 4/1992 | Japan . |
| 5-92026 | 4/1993 | Japan . |

*Primary Examiner*—Geoffrey S. Evans
*Attorney, Agent, or Firm*—Jordan and Hamburg

[57] ABSTRACT

An apparatus permits safe disposal of injection needles by electrically induced heat-generated fusion. The disposal apparatus utilizes a pair of rotating electrodes, spaced apart, and which provide continuously moving points of contact with a needle brought into engagement therewith, and bridging, the electrodes. The moving contact points inhibit electrode degradation. The electrodes are configured and arranged to present a varying size gap between the pair of electrodes, conveniently accomplished by tapering at least one of the electrodes along its length, such that the apparatus can accommodate needles having a wide range of diameters, the needles being inserted between the electrodes where a suitably sized gap exists. The injection needle is inserted into the apparatus such that the needle tip is brought into contact with a first electrode, and a part of the needle closer to the root is brought into contact with the second electrode of the pair. Electrical current is supplied to the electrodes, which fuses the portion of the needle bridging the electrodes because of Joule heat generated by the flowing current. As the needle is pushed farther into the apparatus, the remainder of the length is fused. A scraper may be further provided near one or both electrodes for removing fused materials from the electrodes, to provide additional protection against performance degradation.

21 Claims, 10 Drawing Sheets

INJECTION NEEDLE SAFETY DISPOSAL APPARATUS

CROSS-REFERENCE TO RELATED APPLICATION

This application is a continuation-in-part of U.S. Ser. No. 08/565,427, filed Nov. 30, 1995, now U.S. Pat. No. 5,676,859.

BACKGROUND OF THE INVENTION

The present invention relates to an injection needle safety disposal apparatus. More particularly, it relates to an injection needle safety disposal apparatus wherein the life of the electrode in contact with the injection needle is prolonged and needles are disposed stably, irrespective of the diameter of the needle.

FIG. 16 is an explanatory diagram of an injection needle safety disposal apparatus proposed in the Japanese Patent Laid-open no. 320057/1989 .

A cover 507 of the injection needle safety disposal apparatus 500 is opened and a used needle N is inserted in the insertion slot 502. The injection needle N is retained in the retaining unit 510a of a ring 510, and the tip of the injection needle N touches an electrode 503 supported by a spring 522.

When cover 507 is closed, an electrode 504 clamps the injection needle N because of an interlock, a switch 511 is closed, and electric current flows to the electrodes 503 and 504 through the battery 512. By virtue of this flowing electric current, the injection needle N is heated to a red-hot condition and sterilized. Furthermore, the tip of the injection needle N fuses and becomes rounded. The gas generated when the injection needle is heated to a red-hot condition is led to a deodorizing agent 518 by means of a fan 520, deodorized and discharged. Two to three seconds after electric current flows, the switch 511 switches off automatically.

Next, the ring 510 rotates by 180 degrees, and the treated injection needle N is dropped into a container 516 and destroyed.

Japanese Patent Laid-open no. 126146/1992 proposes an injection needle disposal apparatus wherein the injection needle is fused by using plasma discharge.

Japanese Patent Laid-open no. 92026/1993 proposes an injection needle disposal apparatus wherein the injection needle, softened by passing electric current, is cut by blades.

In the injection needle safety disposal apparatus 500 according to prior art, the fused part of the injection needle is deposited on the contact part 4 of the electrode 504, which is in contact with the injection needle N, causing a performance degradation in the electrode 504. Consequently, frequent replacement of the electrode 504 is necessitated.

Similarly in other injection needle safety disposal apparatus according to prior art, the contact part of the electrode touching the injection needle deteriorates, therefore, necessitating frequent replacement of the electrode.

Another problem is the inability to dispose of the needles stably depending on the diameter of the injection needle.

SUMMARY OF THE INVENTION

The first object of the present invention is to provide an improved injection needle safety disposal apparatus wherein frequent replacement of the electrode is not necessary.

The second object of the present invention is to provide an improved injection needle safety disposal apparatus that allows injection needles to be disposed of stably, irrespective of the diameter of the injection needle.

More specifically, the first aspect of the present invention is to provide an injection needle safety disposal apparatus comprising a first electrode with a contact part that touches the tip of the injection needle, and means to change said contact part. The apparatus further comprises a second electrode with a contact part that touches a part on said injection needle slightly away from the tip and toward the root of the needle, and means the change said contact part. An electrode moving means for moving the first electrode and the second electrode to change the contact part of said first electrode and said second electrode is also provided. The apparatus includes power supply means for supplying power to the first electrode and the second electrode capable of fusing a part of the injection needle when it comes in contact with the first electrode and the second electrode.

In the injection needle safety disposal apparatus according to the aforementioned first aspect, the tip of the injection needle provided in the syringe is brought into contact with the first electrode, and the part slightly away from the tip and toward the root is brought into contact with the second electrode and power is supplied by the power supply means. The part of the injection needle sandwiched between the two electrodes fuses because of Joule heat. By pushing in the syringe so that the tip of the injection needle is always in contact with the first electrode, almost a complete portion of the injection needle can be fused.

By providing means for moving the electrode, the contact part of the electrode touching the injection needle can be continuously moved, and; therefore, the fused part of the injection needle cannot stick to the electrode easily, and degradation in performance of the electrode is prevented. Consequently, the life of the electrode is prolonged and maintenance is facilitated.

The second aspect of the present invention is to provide an injection needle safety disposal apparatus of the aforementioned configuration wherein at least one electrode from the first electrode and the second electrode is a roller-type electrode, and the electrode moving means is a roller-rotation driving means for rotating the roller-type electrode.

In the injection needle safety disposal apparatus according to the aforementioned second aspect, at least one electrode from the first electrode and the second electrode is a roller-type electrode, and means are provided to rotate the roller-type electrodes.

Roller-type electrodes are easy to manufacture and have excellent mechanical strength.

The third aspect of the present invention is to provide an injection needle safety disposal apparatus comprising a first roller-type electrode with constant diameter that touches the tip of the injection needle, and a second roller-type electrode with constant diameter that touches a part on said injection needle slightly away from the tip and toward the root of the needle. Impetus means are provided for giving impetus at least one electrode from the first roller-type electrode and the second roller-type electrode toward the other so that the clearance between the first roller-type electrode and the second roller-type electrode can be adjusted to suit the thickness of the injection needle. Also included are roller-rotation driving means for rotating said first roller-type electrode and the second roller-type electrode, and power supply means for supplying power to the first roller-type electrode and the second roller-type electrode capable of fusing a part of the injection needle when it comes in contact with the first roller-type electrode and the second roller-type electrode.

In the injection needle safety disposal apparatus according to the aforementioned third aspect, the first roller-type electrode of constant diameter and the second roller-type electrode of similar form are used, and an impetus force from the impetus means (for instance, an elastic body) is used to adjust the clearance between the first roller-type electrode and the second roller-type electrode according to the thickness of the injection needle.

As a result, the need to select the location for obtaining the correct clearance to suit the diameter of the injection needle is eliminated, and even a worker with no knowledge of the diameter of the injection needle can dispose of the injection needles conveniently. Moreover, since the roller-type electrode has a simple cylindrical shape, manufacture of roller-type electrodes is easy.

The fourth aspect of the present invention is to provide an injection needle safety disposal apparatus of the aforementioned configuration comprising means for scraping off material deposited on the electrode, which is provided at least near one of the electrodes from the first electrode and the second electrode.

In the injection needle safety disposal apparatus according to the aforementioned fourth aspect, means for scraping off material deposited on the electrode are provided at least near one of the electrodes from the first electrode and the second electrode.

By providing such means, even if a fused part of the injection needle sticks to the electrode, it is scraped off before it hardens, and therefore, degradation in performance of the electrode is prevented. Consequently, the life of the electrode is prolonged and maintenance thereof is facilitated.

The fifth aspect of the present invention is to provide an injection needle safety disposal apparatus of the aforementioned configuration comprising covering means configured such that when an injection needle is inserted in an injection needle insertion hole into which an insertion need can be inserted, a base of the syringe provided with an injection needle adheres closely, isolating the outside of the injection needle safety disposal apparatus from the inside. The covering means moves up or down following the motion of the syringe when said syringe is pushed in or pulled out.

In the injection needle safety disposal apparatus according to the aforementioned fifth aspect, the covering means provided enables the base of the syringe to adhere closely, isolating the outside of the injection needle safety disposal apparatus from the inside, and the covering means moves up or down following the motion of syringe when the syringe is pushed in or pulled out.

Although sparks are generated when the injection needle and electrodes come in contact, by providing the covering means, the sparks cannot leak outside the injection needle safety disposal apparatus, and safety is improved.

The sixth aspect of the present invention is to provide an injection needle safety disposal apparatus of the aforementioned configuration comprising a tray which can receive and collect fused and hardened materials that drop after they are generated when a part of the injection needle fuses, and which can be removed easily from the injection needle safety disposal apparatus. A safety switch means for disabling the power supply means which supplies power to said first electrode and second electrode for fusing a part of the injection needle is provided, operable in response to a condition in which the tray has been removed from the injection needle safety disposal apparatus.

In the injection needle safety disposal apparatus according to the aforementioned sixth aspect, the tray, which can receive and collect metal scrap generated when a part of the injection needle fuses and which can be removed easily from the injection needle safety disposal apparatus, are provided. In addition, safety switch means, which disables supply of power when the tray has been removed from the injection needle safety disposal apparatus, are also provided.

If the tray means is removed for discarding the scrap, and subsequently, if re-fitting of the tray has not been implemented, the injection needle safety disposal apparatus will not operate. Therefore, the safety switch means ensures that the re-fitting of the tray is not forgotten.

The seventh aspect of the present invention is to provide an injection needle safety disposal apparatus of the aforementioned configuration comprising deodorizing means communicative with exhaust means for discharging the air in the vicinity of the electrodes after it has been led to the deodorizing means and deodorized, said exhaust means being a positive-displacement-type pump.

In the injection needle safety disposal apparatus according to the aforementioned seventh aspect, a positive-displacement-type pump is used as the exhaust means for discharging the air in the vicinity of the electrodes after it has been led to the deodorizing means and deodorized.

In the past, axial flow fans and centrifugal fans were used as exhaust means, but adequate static pressure cannot be obtained in turbo pumps such as axial flow fans and centrifugal fans. Therefore, an adequate amount of deodorizing agents could not be passed through, resulting in traces of odors of burnt blood. In contrast, in the present invention, a positive-displacement-type pump such as reciprocating pump or rotary pump is used as exhaust means, and therefore, static pressures (for instance, equal to or greater than 100 $mmH_2O$) that is much higher than the exhaust resistance (for instance, about 30 $mmH_2O$) of the existing exhaust equipments generally used are obtained. Consequently, adequate quantity of deodorizing agents can be passed through, resulting in satisfactory deodorization.

The eighth aspect of the present invention is to provide an injection needle safety disposal apparatus of the aforementioned configuration comprising auxiliary power supply means for supplying power to the electrode moving means or the roller-rotation driving means in the injection needle safety disposal apparatus.

In the aforementioned configuration, it is recommended that the auxiliary power supply means be charged by the supply voltage from the power supply means.

In the injection needle safety disposal apparatus according to the aforementioned eighth aspect, since the power from the auxiliary power supply means can be supplied to the electrode moving means or the roller-rotation driving means, even if the voltage of the power supply means drops when a large current flows for fusing the injection needle, the electrode moving means and the roller-rotation driving means will not stop, enabling steady and continuous disposal of injection needles.

Moreover, if an arrangement to charge the auxiliary power supply means by the supply voltage from the power supply means is used, the auxiliary power supply means can be automatically charged when the supply voltage to the power supply means is restored, thereby eliminating the inconvenience of charging the auxiliary power supply means manually.

DETAILED DESCRIPTION OF THE INVENTION

The present invention will hereinafter be described in more detail with reference to the embodiments shown in the figures. However, it must be understood that these embodiments are intended to illustrate the invention and are not to be construed to limit the scope of the invention.

First Embodiment

Figure 1:
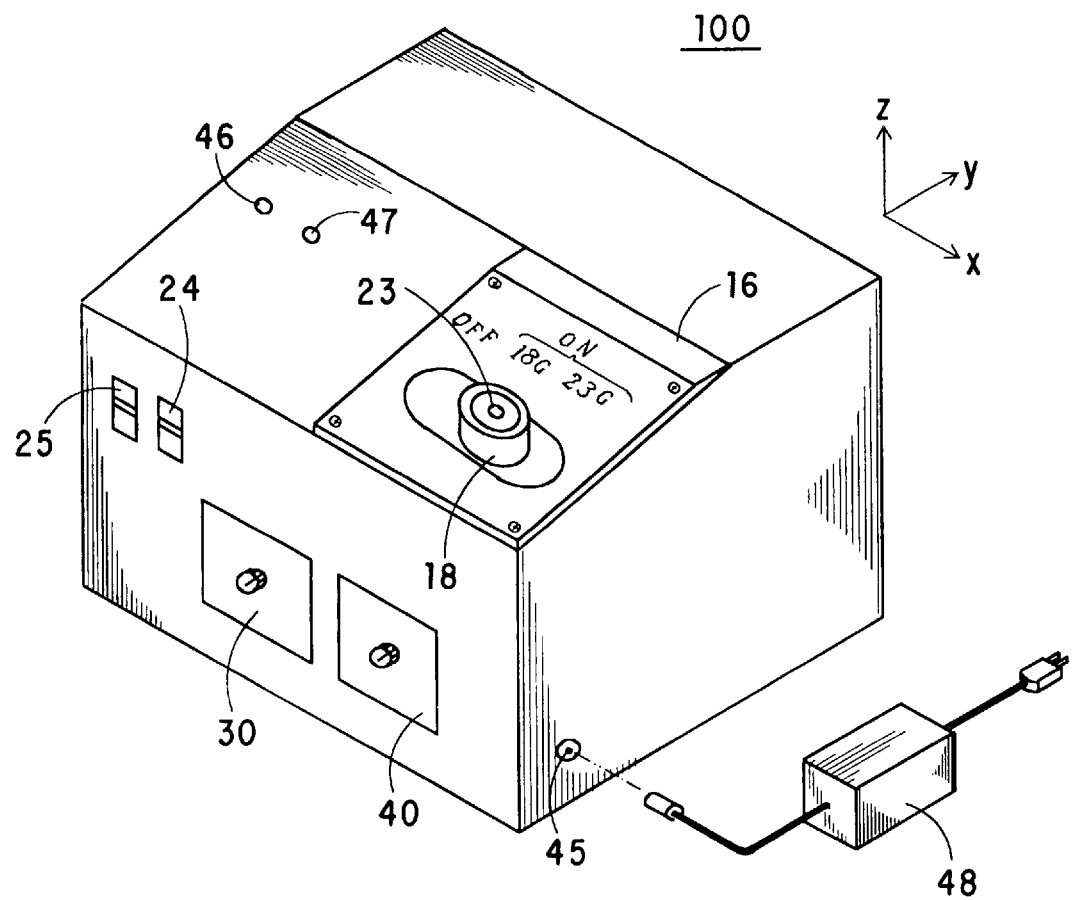
FIG. 1 is an external view showing the injection needle safety disposal apparatus according to the first embodiment of the present invention.

FIG. 1 is an external view of the injection needle safety disposal apparatus 100 in the first embodiment of the present invention. For the purpose of explanation, the transverse direction is taken as the x direction; the depth direction is taken as the y direction; and the vertical direction is taken as the z direction.

On the upper face of the injection needle safety disposal apparatus 100 is provided a panel 16, a power supply lamp 46, and a charging indicator lamp 47. A cylinder 18 protrudes from the panel 16. The cylinder 18 can move in the x direction. If it moves to the end of left, the power supply of the injection needle safety disposal apparatus 100 is opened and turned OFF if it moves toward the right side, the power supply of the injection needle safety disposal apparatus 100 is closed and turned ON. A scale calibrated to relate the position of cylinder 18 and diameter of the injection needle is printed on the panel 16. The farther the position of cylinder 18 to the right, the smaller is the diameter of the injection needle. An injection needle insertion hole 23 for inserting the injection needle is provided in the cylinder 18.

On the front face of the injection needle safety disposal apparatus 100 is the exposed drawer face of a tray 40, which is used to receive and collect the metal scrap generated when the injection needle is fused. The front face of the injection needle safety disposal apparatus 100 also presents the exposed drawer face of a deodorizing unit 30, which deodorizes the gas generated when the injection needle is fused; a reset switch 24 for the circuit protector (44 of FIG. 8) used as a circuit breaker when excess electric current flows; and a reverse rotation switch 25 for reversing the direction of rotation of roller-type electrodes (5, 6 in FIG. 3) described later.

A charging jack 45 for connecting a charger 48 is provided on the side face of the injection needle safety disposal apparatus 100.

Instead of the charging indicator lamp 47, a battery checker meter may be alternatively installed for analog detection of output voltages of battery (described later). This option has the advantage of accurately indicating the required level of charge when charging the battery.

Figure 2:
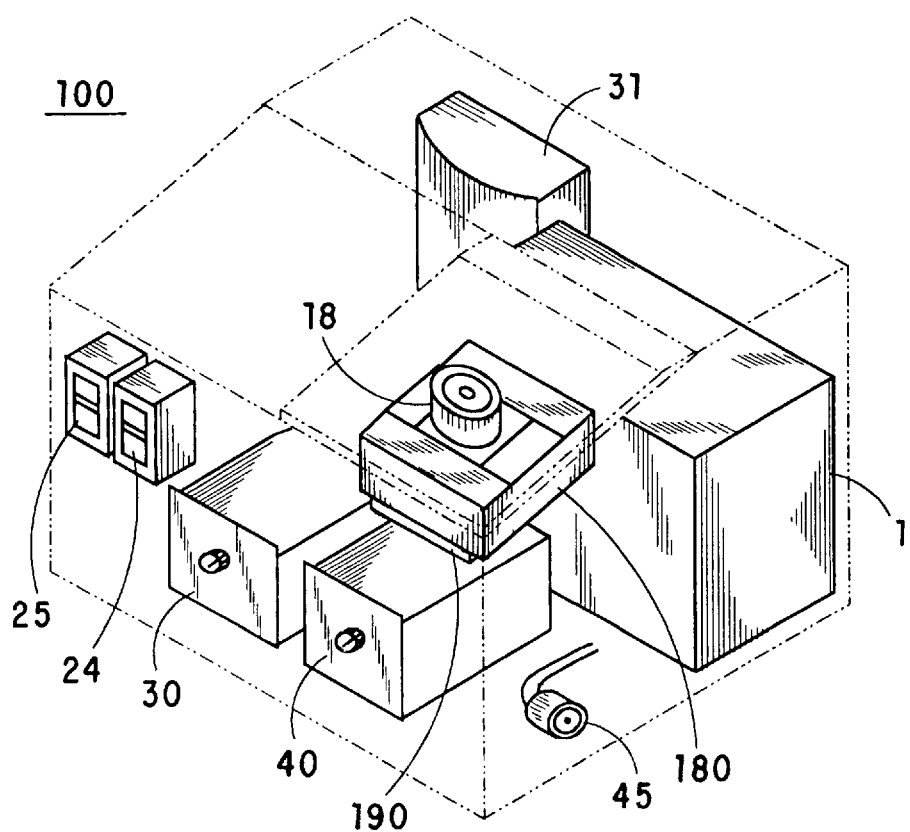
FIG. 2 is a perspective view showing the internal construction of the injection needle safety disposal apparatus of FIG. 1.

FIG. 2 is a perspective view showing the internal construction of the injection needle safety disposal apparatus 100.

A movable unit 180, which enables movement of the cylinder 18 in the x direction, is installed directly below the cylinder 18. The composition and operation of the movable unit 180 are explained later with reference to FIG. 3 and FIG. 5.

An electrode unit 190 for fusing the injection needle is installed directly beneath the movable unit 180. The composition and operation of the movable unit 190 are explained later referring to FIG. 3 and FIG. 4.

An exhaust unit 31 for collecting and discharging air in said electrode unit 190 after it has passed through the deodorizing unit 30, is installed on the rear face of the injection needle safety disposal apparatus 100.

A battery 1 which supplies power for fusing the injection needle is installed on the rear face of the injection needle safety disposal apparatus 100.

Figure 3:
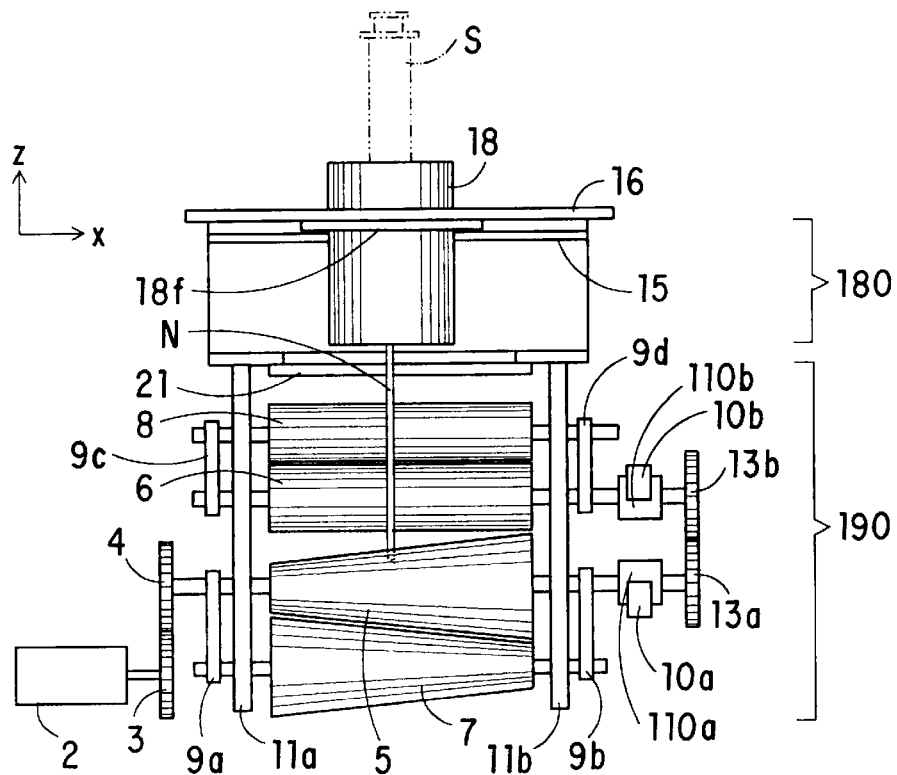
FIG. 3 is an explanatory drawing of the movable unit and the electrode unit.

FIG. 3 is an explanatory drawing of the movable unit 180 and the electrode unit 190.

A guide plate 15 in the movable unit 180 supports only the protruding part in the y direction of flange 18f, which protrudes from the cylinder 18. This arrangement enables the flange 18f to slide on the guide plate 15 in the x direction so that cylinder 18 can move in the x direction.

A spark arresting film 21 is affixed on the base of the movable unit 180.

First roller-type electrode 5 and second roller-type electrode 6 are provided in the electrode unit 190. The first roller-type electrode 5 has a tapered shape so that its diameter varies along the direction of the axis of rotation. The second roller-type electrode has a constant diameter throughout the direction of the axis of rotation. The axis of rotation of the first roller-type electrode 5 and the axis of rotation of the second roller-type electrode 6 are parallel to each other. Therefore, the gap between the surface of the first roller-type electrode 5 and the second roller-type electrode 6 becomes smaller when moving from left to right along the direction of the axis of rotation. If the cylinder 18 is positioned to match the scale of the panel 16, the narrow space between the surfaces of roller-type electrodes 5 and 6 can be used for thin injection needles, and the wide space between the surface of roller-type electrodes 5 and 6 can be used for thick injection needles.

Materials with small electrical resistance, such as brass or phosphor bronze are recommended as the material for central shafts of the roller-type electrodes 5 and 6. For circumferential surfaces (the parts of the electrode surface that touch the injection needle N) of the roller-type electrodes 5 and 6, materials with small electrical resistance, high melting point, good thermal conductivity are recommended, such as titanium, tungsten, or alloys of materials (for instance, brass or phosphor bronze) containing tungsten and copper or silver. To manufacture the roller-type electrodes 5 and 6, the circumferential surface may be wrapped around the central shaft, or it may be manufactured in pipe form and press fit onto the central shaft which is inserted therein.

The central shafts of the roller-type electrodes 5 and 6 are provided with slip rings 110a and 110b. The slip rings 110a and 110b are in contact with brushes 10a and 10b to which power is supplied from the battery 1. As a result, power from the battery 1 is supplied to the roller-type electrodes 5 and 6 through brushes 10a and 10b, and slip rings 110a and 110b. If the inner surfaces of slip rings 110a and 110b and the surfaces of shafts of the roller-type electrodes 5 and 6 are designed to slide, then both surfaces should preferably be hard-chrome-plated to reduce friction.

The first roller-type electrode 5 is driven and rotated by a DC motor 2 through gears 3 and 4. The second roller-type electrode 6 is driven and rotated by a DC motor 2 through gears 3 and 4, the first roller-type electrode 5 and gears 13a and 13b.

A scraper 7 is provided near the first roller-type electrode 5 for scraping off material deposited on the first roller-type electrode 5. The first roller-type electrode 5 and the scraper 7 are connected by circular belts 9a and 9b, and they rotate in opposite directions with respect to each other. This arrangement enables fused material to be scraped off efficiently.

Also, a scraper 8 is provided near the second roller-type electrode 6 for scraping off material deposited on the second roller-type electrode 6. The second roller-type electrode 6 and the scraper 8 are connected by circular belts 9c and 9d, and they rotate in opposite directions with respect to each other. This arrangement enables fused material to be scraped off efficiently.

The roller-type electrodes 5 and 6, and the scrapers 7 and 8 are supported by support plates 11a and 11b. Use of heat resistant plastics (for instance, thermoplastic polyester based composite sheet) is recommended for said support plates 11a and 11b because heat is transferred thereto from the roller-type electrodes 5 and 6.

The support plates 11a and 11b are fitted such that they can be removed from the movable unit 180. If the support plates 11a and 11b are removed from the movable unit 180, the roller-type electrodes 5 and 6, and scrapers 7 and 8 can be removed. Therefore, maintenance such as cleaning or replacement of these items is facilitated.

The injection needle N of the syringe S inserted in the cylinder 18 passes through the cylinder 18. The tip of the injection needle N touches the first roller-type electrode 5. The part of the injection needle N slightly away from the tip and toward the root touches the second roller-type electrode 6. The part of the injection needle N that touches the roller-type electrodes 5 and 6 generates Joule heat because of the flow of a large electric current, fuses and falls off. The resultant metal scrap is received and collected in the tray 40. At this stage, in order to position the cylinder 18 to match the scale of the panel 16, if the diameter of the injection needle N is small, the gap between the parts in contact with roller-type electrodes 5 and 6 decreases. If the diameter of the injection needle is large, the gap between the parts in contact with roller-type electrode 5 and 6 increases. The resistance value of the part of the injection needle N in contact with the roller-type electrodes 5 and 6 is small if the injection needle N is thick rather than thin when the diameter is considered; however, this value becomes large if the gap is large rather than small when the gap is considered. Therefore, the resistance value does not change appreciably even if the diameter of the injection needle N changes, and the electric current does not flow excessively or poorly, irrespective of the diameter of the injection needle, enabling stable disposal of the injection needle.

Figure 4:
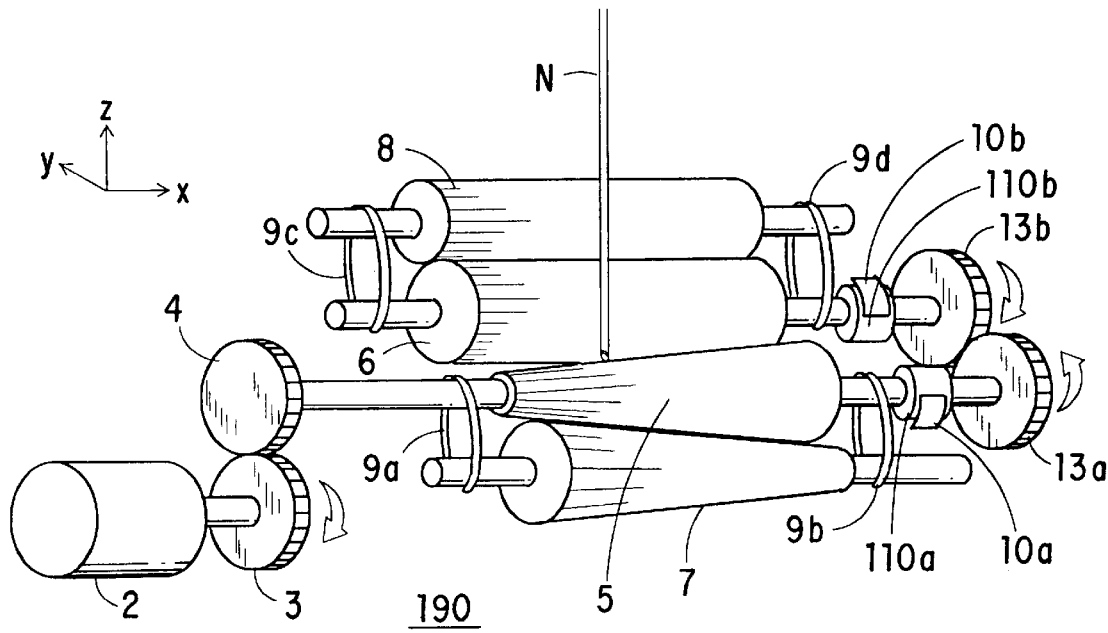
FIG. 4 is a perspective view of the major parts of the electrode unit.

FIG. 4 is a perspective view of the major parts of the electrode unit 190.

The direction of rotation of roller-type electrodes 5 and 6 is such that the injection needle N is pulled in. The direction of rotation is shown by arrows in the figure.

Figure 5:
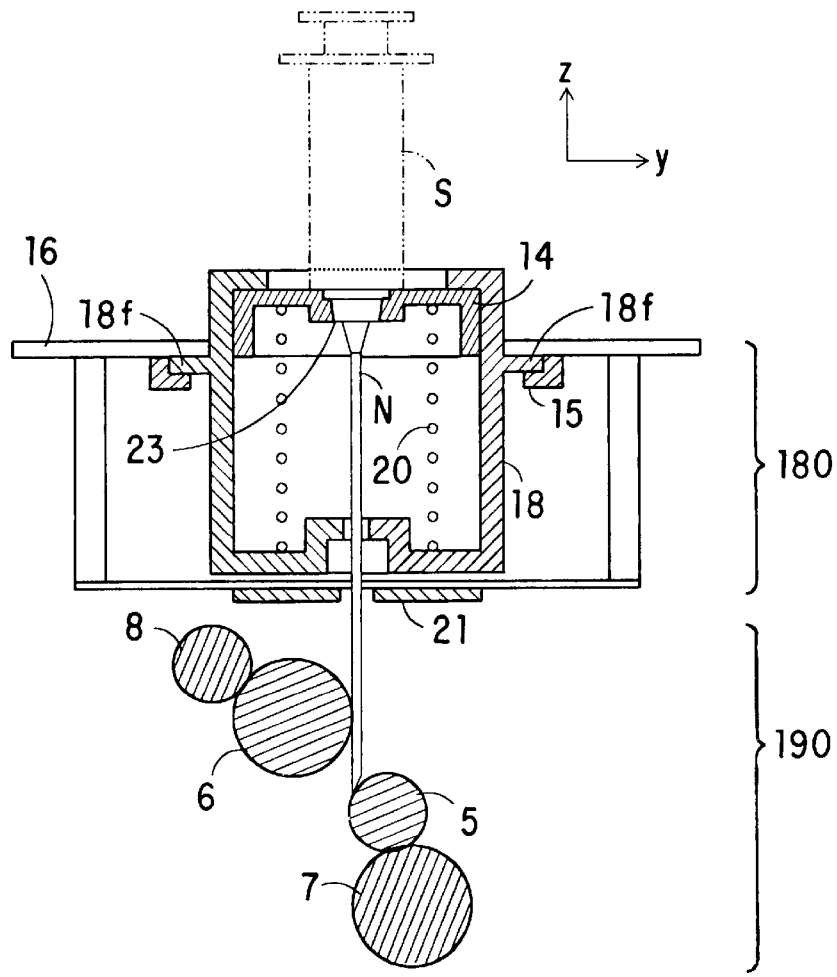
FIG. 5 is a cross-section view showing the internal construction of the cylinder.

FIG. 5 is a cross-section view showing the internal construction of the cylinder 18.

A cover 14 provided inside the cylinder 18 and is capable of motion in the vertical direction, and is supported by a spring 20. An injection needle insertion hole 23 is drilled in the cover 14. Consequently, when the injection needle N of the syringe S is inserted in the injection needle insertion hole 23, the base of the syringe S adheres closely to the cover 14. When the injection needle N touches the roller-type electrodes 5 and 6, sparks are generated, but since these sparks cannot leak out of the injection needle safety disposal apparatus 100, safety is improved.

During the disposal of the injection needle N, the operator pushes the syringe S inward against the resistive, upwardly biasing elastic forces of the spring 20, with the base of the syringe S adhering closely to the cover 14. Thereupon, the tip of the injection needle N initially touches the second roller-type electrode 6, and then touches the first roller-type electrode 5. Consequently, electric current flows and the tip of the injection needle N is fused. The operator pushes the syringe S in further, and the complete injection needle except for a very small part becomes fused and gets converted to metal scrap. The base of the injection needle N fuses and seals off the space, preventing leakage of residue in the syringe S.

Since the roller-type electrodes 5 and 6 are rotating during this process, the parts in contact with the injection needle N change all the time. Moreover, the scrapers 7 and 8 scrape off fused material as soon as it is formed. Therefore, deposition of part of the injection needle N is prevented, degradation of the performance of roller-type electrodes 5 and 6 is prevented, and the life of the electrode is prolonged.

If the roller-type electrodes 5 and 6 are rotated such that the injection needle N is pulled inward, it becomes easy to push the syringe S in with minimal force. If the injection needle N is stuck between the roller-type electrodes 5 and 6 because of a drop in the voltage of the battery 1, the direction of rotation of the electrodes can be reversed by means of the reverse rotation switch 25, and the injection needle N can be pulled out.

Figure 6:
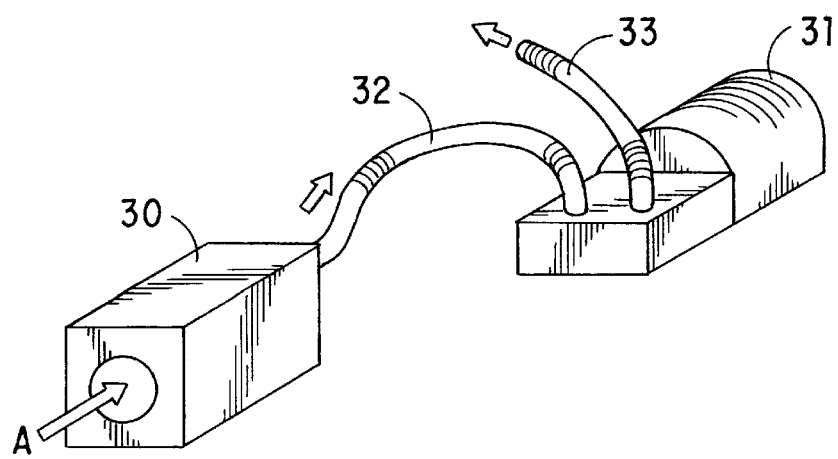
FIG. 6 is an explanatory drawing of the deodorizing unit and the exhaust unit.

FIG. 6 is an explanatory drawing showing the deodorizing unit 30 and the exhaust unit 31.

The deodorizing unit 30 contains deodorizing agents such as activated charcoal, open cellular urethane sheet containing activated charcoal, fibrous activated charcoal, or non-woven fabric either independently or as a combination of these substances. The deodorizing unit 30 can be removed easily from the injection needle safety disposal apparatus 100 (refer to FIG. 1 and FIG. 2), and therefore, the deodorizing agent can be replaced easily.

The exhaust unit 31 sucks air A in the electrode unit 190 through the deodorizing unit 30 and an air intake pipe 32, and discharges it outside the injection needle safety disposal apparatus 100 through an exhaust pipe 33. A positive-displacement type blower or compressor is recommended for use as the exhaust unit 31 rather than a turbo type blower or compressor. This is because the former is compact and is capable of easily producing high compression (for instance, obtaining a static pressure equal to or greater than 100 mmH$_2$O), and therefore, without sacrifice of the compactness of the injection needle safety disposal apparatus 100, foul odors in the apparatus and gases generated during the fusion of the injection needle can be satisfactorily absorbed and deodorized using deodorizing agents.

By deodorizing and discharging the air and gases generated when the injection fluid or blood residue in the injection needle N is burnt, the spread of foul odors can be prevented.

Figure 7:
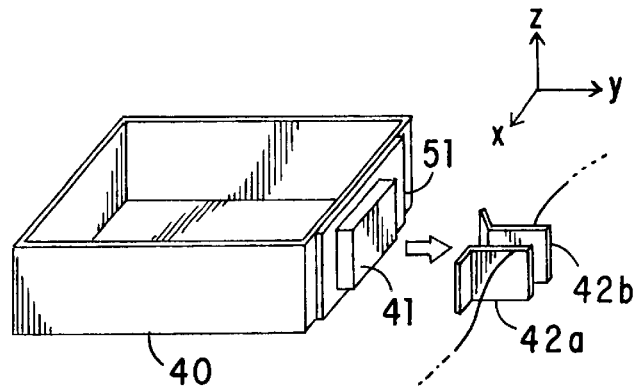
FIG. 7 is an explanatory drawing of the safety switch.

FIG. 7 is an explanatory drawing of the rear face of the tray 40.

An insulated plate 51 is affixed to the rear face of the tray 40. A conductive contact block 41 is fitted to the insulated plate 51.

A pair of contact plates 42*a* and 42*b* are provided inside the injection needle safety disposal apparatus 100. When the tray 40 is fully inserted, the contact block 41 connects the contact plates 42*a* and 42*b* making them conductive with one another. The function of a safety switch is realized by using this mechanism (described later). Instead of the above described mechanism, a limit switch (commercially available) that switches to an OFF position when the tray 40 is pulled out, can also be used to accomplish the function of a safety switch.

Figure 8:
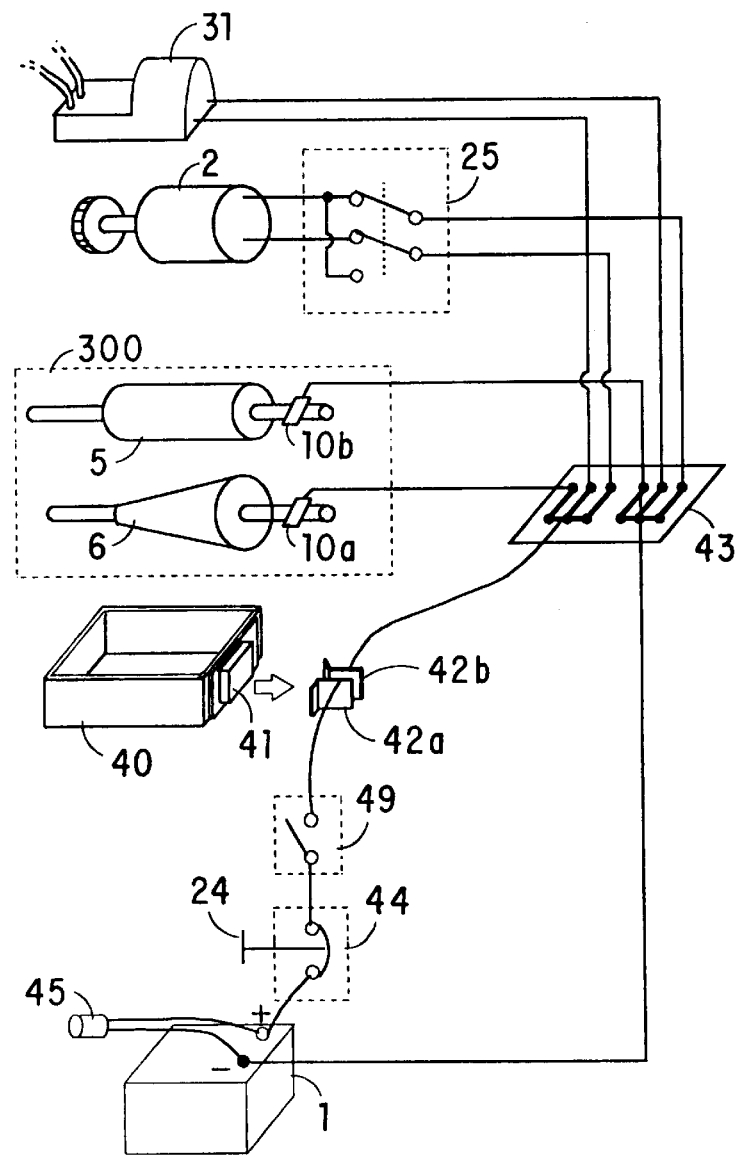
FIG. 8 is a wiring diagram of the injection needle safety disposal apparatus of FIG. 1.

FIG. 8 is the wiring diagram of the injection needle safety disposal apparatus 100.

The battery 1 is connected to a terminal block 43 through a circuit protector 44, a main switch 49 (this is a switch interlocked with the position of the cylinder 18), and contact plates 42*a* and 42*b*.

The terminal block 43 is connected to brushes 10*a* and 10*b*. The terminal block 43 is also connected to DC motor 2 through the reverse rotation switch 25. The terminal block 43 is also connected to the exhaust unit 31.

Second Embodiment

Figure 9:
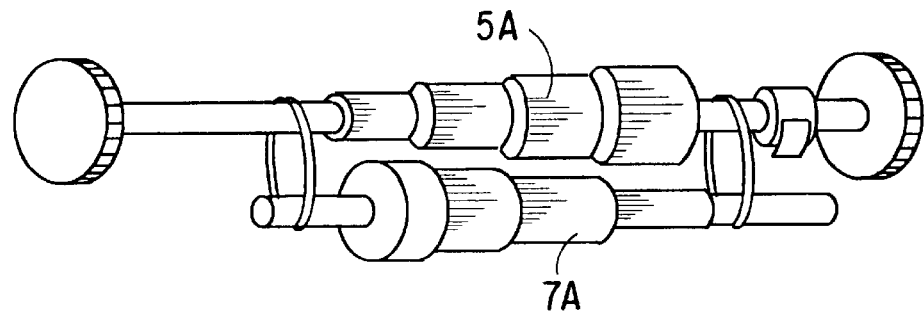
FIG. 9 is a perspective view of the roller-type electrode of the second embodiment of the present invention.

Instead of the tapered shape roller-type electrode 5 and scraper 7 (refer to FIG. 4), a roller-type electrode 5A and a scraper 7A each of which is provided with steps as shown in FIG. 9 may also be used.

This embodiment advantageously increases the range in the x direction for disposing needles of various thicknesses (23G, 21G, 18G, 16G, etc.).

Third Embodiment

Figure 10:
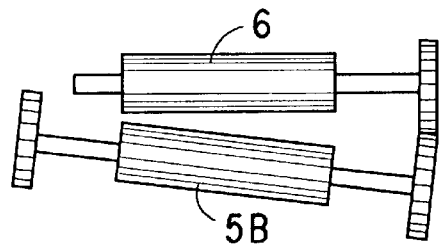
FIG. 10 is an explanatory drawing of the arrangement of roller-type electrodes of the third embodiment of the present invention.

A first roller-type electrode 5B of cylindrical shape with constant diameter and inclined with respect to the roller-type electrode 6 may also be used, as shown in FIG. 10.

This embodiment advantageously eliminates the need to use the roller-type electrode 5 with a taper, which is difficult to manufacture.

Fourth Embodiment

Figure 11:
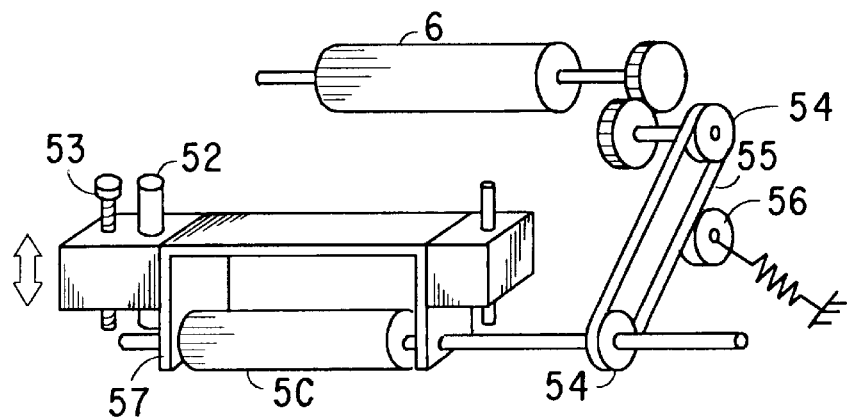
FIG. 11 is a perspective view showing the construction of roller-type electrodes of the fourth embodiment of the present invention.

As shown in FIG. 11, an arrangement wherein, a first roller-type electrode 5C of cylindrical shape with constant diameter is supported by a support fitting 57 capable of motion along a guide shaft 52 by means of a gap adjustment screw 53, thereby enabling the gap between the first roller-type electrode 5C and the second roller-type electrode 6 to be adjusted, may also be provided. Rotation can be transferred to the second roller-type electrode 6 through pulleys (or sprockets) 54, a timing belt (or chain) 55, and an idler roller 56.

This embodiment advantageously allows the operator to easily set a gap that is optimum for the thickness of the injection needle.

Fifth Embodiment

Figure 12:
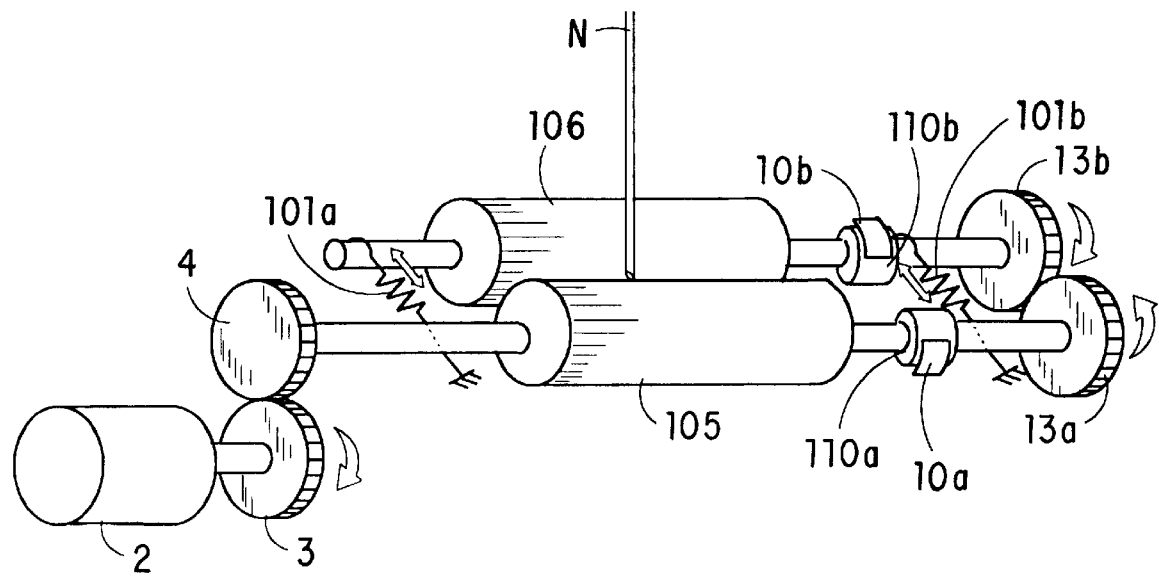
FIG. 12 is a perspective view showing the construction of roller-type electrodes of the fifth embodiment of the present invention.

As shown in FIG. 12, an arrangement comprising a first roller-type electrode 105 with fixed axis of rotation, a second roller-type electrode 106 with axis of rotation movable toward the first roller-type electrode 105 within the range of engagement margin of gear 13*a* and gear 13*b*, and tension springs 101*a* and 101*b*, which provide impetus by biasing the second roller-type electrode 106 toward the first roller-type electrode 105 may be used (such an arrangement for providing moving means to the axis of the roller-type electrode not directly rotated by the DC motor 2 is recommended). The roller-type electrodes 105 and 106 have cylindrical form with constant diameter in the direction of the axis of rotation.

As a result, when the injection needle N is inserted between the roller-type electrodes 105 and 106, the clearance between the roller-type electrodes 105 and 106 is automatically adjusted according to the thickness of the injection needle N and can be made constant both contact pressure regardless of thickness of the injection needle N. It is recommended that injection needles N with diameters in the range of 0.65 mm to 1.6 mm be processed considering the margin of engagement of gears 13*a* and 13*b*.

Since positioning the cylinder (equivalent to 18 in FIG. 3) to obtain the correct clearance to suit the diameter of the injection needle N is not necessary, the arrangement described above provides the advantage that injection needles N can be disposed off satisfactorily even by a worker who has no knowledge about the diameter of the injection needle N. Another advantage is that there is no need for using the tapered roller-type electrode 5, which is difficult to manufacture, or the roller-type electrode 5A, which contains steps.

Sixth Embodiment

Figure 13:
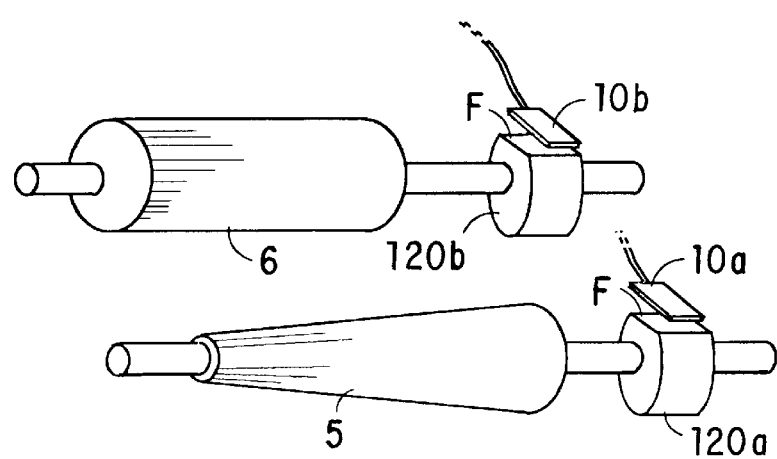
FIG. 13 is an explanatory drawing of the slip ring of the sixth embodiment of the present invention.

Cam-shaped slip rings 120*a* and 120*b* provided with notched parts F, as shown in FIG. 13 may also be used.

At the notched parts F, the brushes 10*a* and 10*b* and the slip rings 120*a* and 120*b* break contact (or the contact pressure becomes local resulting in an increase in contact resistance), therefore an intermittent pulse electric current (or a periodically small electric current) can be made to flow to the injection needle. Since the power consumption is reduced, the life of the battery 1 can be prolonged by this arrangement. Moreover, since a small electric current is used, damage to the roller-type electrode 5 and 6 can also be reduced.

Seventh Embodiment

Figure 14:
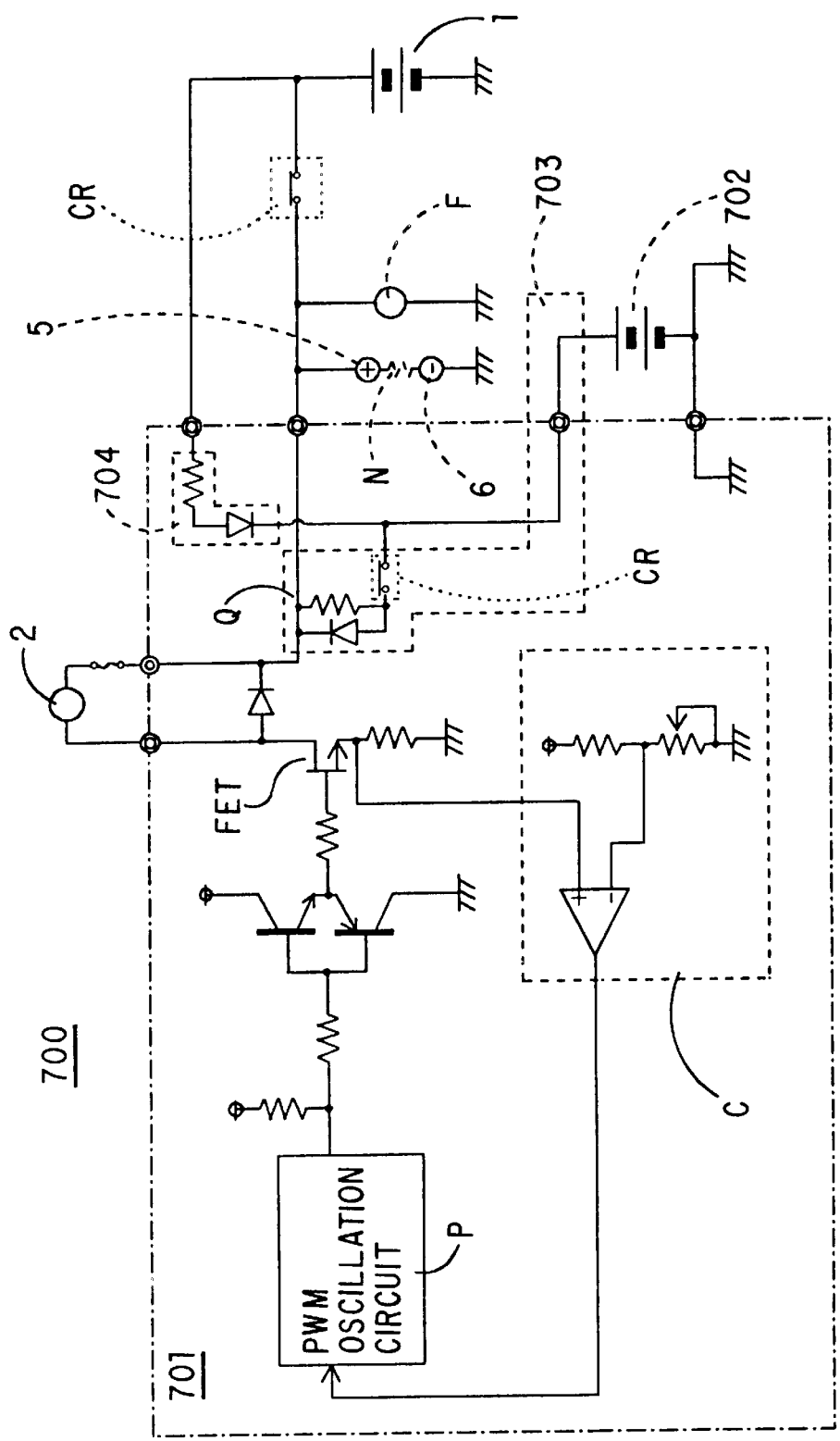
FIG. 14 is a circuit diagram of the injection needle safety disposal apparatus of the seventh embodiment of the present invention.

FIG. 14 shows the circuit diagram of the injection needle safety disposal apparatus illustrating the seventh embodiment of the present invention.

In the injection needle safety disposal apparatus 700, power from battery 1 is supplied to the roller-type electrodes 5 and 6 (refer to FIG. 4) sandwiching the injection needle N, and to the positive-displacement-type blower (or compressor) F used in the exhaust unit 31 (refer to FIG. 6). Power is also supplied to the control board 701, after passing through main switch CR provided with an overcurrent protection function.

In the control board 701, the power is supplied to DC motor 2 for rotating the roller-type electrodes 5 and 6. The PWM (Pulse Width Modulation) oscillation circuit P feeds back pulse signals of pulse width matching that of the driving current of DC motor 2 detected by the current detecting comparator C to the FET, and stabilizes the rotation of DC motor 2.

The seventh embodiment of the injection needle safety disposal apparatus 700 advantageously comprises an auxiliary battery 702, an auxiliary power supply circuit 703 that supplies power from the auxiliary battery 702 to the control board 701, and the charging circuit 704 that charges the auxiliary battery 702.

In an embodiment that does not include the auxiliary battery 702, a large current flows from the battery 1 during the fusing of the injection needle N, and the supply voltage drops. Consequently, if the DC motor 2 stops temporarily, an overcurrent flows to the DC motor 2, the main switch CR with the overcurrent protection function opens, and the complete operation stops. In contrast, in the seventh embodiment, when a large current flows from the battery 1 and the supply voltage (voltage at Q in FIG. 14) to the DC motor 2 drops, power is supplied from the auxiliary battery 702 to the DC motor 2 through the auxiliary power supply circuit 703, thereby preventing the temporary stoppage of the DC motor 2. Consequently, the stoppage of the complete operation because of the opening of the main switch CR provided with the overcurrent protection function is prevented. Moreover, if the output voltage of the auxiliary battery 702 drops, a charging current flows to the auxiliary battery 702 through the charging circuit 704 when the supply voltage from the battery 1 is restored, and charges the auxiliary battery 702. (However, the forward voltage of the diode in the charging circuit 704 is ignored.) Consequently, the inconvenience of charging the auxiliary battery 702 manually is eliminated.

Eighth Embodiment

Figure 15A:
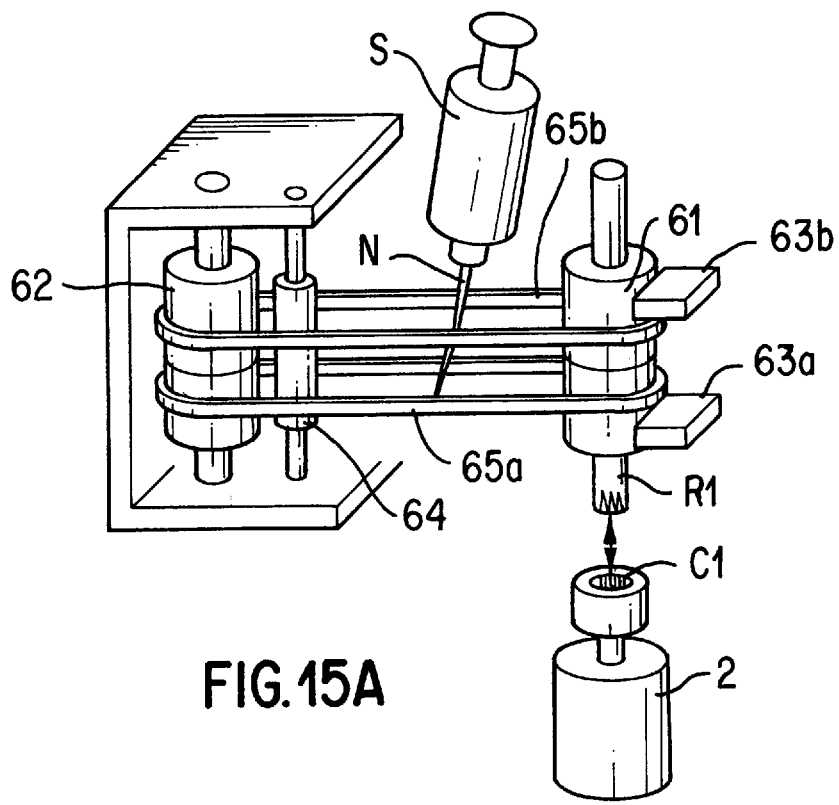
FIG. 15A and FIG. 15B are explanatory drawings of the electrode unit of the eighth embodiment of the present invention.
Figure 15B:
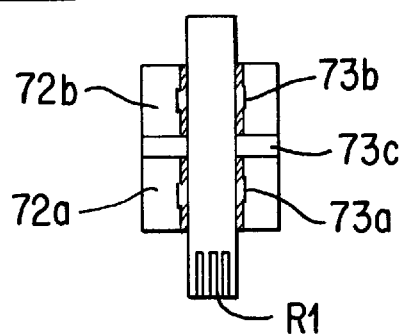
Figure 16:
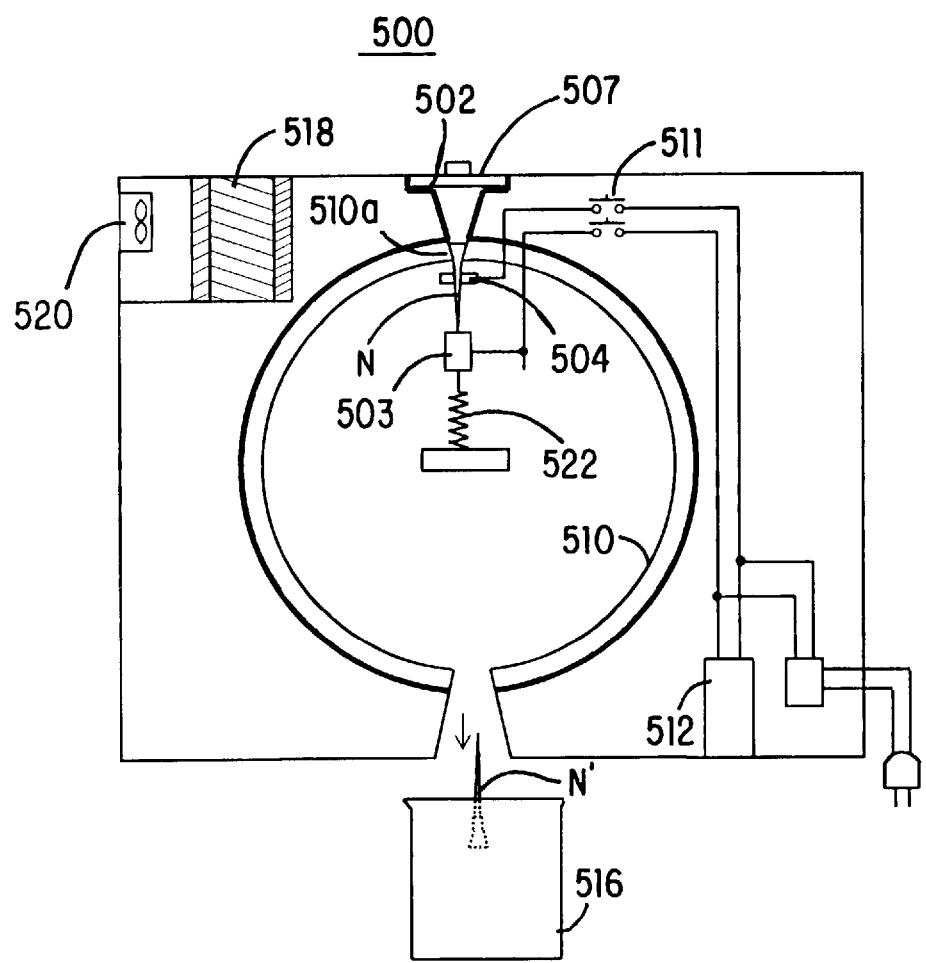
FIG. 16 is an explanatory drawing showing an example of the injection needle safety disposal apparatus of prior art.

As shown in FIG. 15A, metal wires (or metal belts) 65a and 65b are stretched between a pair of rollers 61 and 62. Rollers 61 and 62, as shown in a cross-section view in FIG. 15B, and contact parts 72a and 72b of metal wires 65a and 65b, are made of a conducting metal. Also, the contact parts 72a and 72b are insulated by means of insulated sleeves 73a and 73b, and insulated disc 73. Contacts 63a and 63b are brought in close contact with the contact parts 72a and 72b and power is supplied.

The injection needle N of the syringe S is inserted between the metal wires 65a and 65b. The tip of the injection needle N is brought into contact with the internal surface of the metal wire 65a at the front.

Power is supplied through the metal wires 65a and 65b, thus enabling fusing of the injection needle N.

The roller 61 is rotated by engagement of serration R1 in the roller 61 with the coupling C1 fitted to DC motor 2. A file 64 scrapes off material deposited on the metal wires 65a and 65b. This enables the life of the metal wires 65a and 65b to be prolonged.

If the diameter of the roller 61 is made different from the diameter of the roller 62, the gap between the internal surface of the metal wire 65a at the front side and the internal surface of the metal wire 65b at the far side will vary depending on the position, and therefore various thicknesses of injection needle N can be used.

Ninth Embodiment

A torque limiter may be fitted on the rotating shaft of gear 3 of DC motor 2, and the DC motor made to rotate only in one direction without providing the reverse rotation switch 25. According to this embodiment, when the injection needle is at the point of being engaged between roller-type electrodes 5 and 6, since the DC motor 2 is running idle, the injection needle is no longer engaged with a strong force. Moreover, the injection needle can be pulled out easily.

Tenth Embodiment

A pulse motor may be used instead of the DC motor 2.

Generally, the brush which provides a slidable contact in the DC motor 2 wears away due to mechanical contact and its life is shortened comparatively. Moreover, since it is difficult to obtain low rotating speed (for instance, 100 rpm) of the motor itself, the high rotating speed has to be reduced by means of gear mechanisms, which results in relatively noisy operation.

In contrast, the life of a pulse motor is prolonged because of the brushless mechanism used. Special gear mechanisms are not required, and low rotating speed can be obtained in the motor itself, therefore the operating noise can be held to a minimum. Moreover, since the torque required for rotating the roller-type electrodes (ex. 5, 6 in FIG. 4) is not very high, adequate rotating force can be obtained when the pulse motor is used.

In this way, according to the present invention of the injection needle safety disposal apparatus, by moving the electrodes, the parts of electrodes in contact with the injection needle can be continuously varied so that deposition of the fused part of the injection needle on the electrode is inhibited. As a result, degradation in performance of electrode is prevented, and the life of the electrode is prolonged and maintenance is facilitated.

What is claimed is:

1. An injection needle safety disposal apparatus comprising:
   a first roller electrode with constant diameter that touches the tip of the injection needle;
   a second roller electrode with constant diameter that touches a part on said injection needle slightly away from the tip and toward the root of the needle;
   impetus means for giving impetus at at least one roller electrode of said first roller electrode and said second roller electrode toward the other roller electrode so that the clearance between said first roller electrode and said second roller electrode can be adjusted to suit the thickness of the injection needle;
   roller-rotation driving means for rotating said first roller electrode and said second roller electrode;
   power supply means for supplying power to said first roller electrode and said second roller electrode capable of fusing a part of said injection needle when it comes in contact with said fist roller electrode and said second roller electrode.

2. An injection needle safety disposal apparatus of claim 1 comprising;
   means for scraping off material deposited on the electrode, which is provided at least near one of the electrodes from said first electrode and said second electrode.

3. An injection needle safety disposal apparatus of claim 2 further comprising:
   auxiliary power supply means for supplying power to said roller-rotation driving means in the injection needle safety disposal apparatus.

4. An injection needle safety disposal apparatus of claim 1, further comprising:
   a cover including an injection needle insertion hole into which an injection needle can be inserted, said cover being configured such that a base of a syringe provided with said injection needle adheres closely therewith, isolating the outside of the injection needle safety disposal apparatus from the inside, said cover being movable up or down following the motion of the syringe when said syringe is pushed in or pulled out.

5. An injection needle safety disposal apparatus of claim 4, further comprising:
   auxiliary power supply means for supplying power to said electrode moving means in the injection needle safety disposal apparatus.

6. An injection needle safety disposal apparatus of claim 1, further comprising:

a tray removable from a remainder of the injection needle safety disposal apparatus, said tray including means for receiving and collecting fused and hardened materials that drop after they are generated when a part of the injection needle fuses; and safety switch means for disabling said power supply means, which supplies power to said first electrode and second electrode for fusing a part of the injection needle, said safety switch means operable in response to a condition in which said tray is removed from said remainder of the injection needle safety disposal apparatus.

7. An injection needle safety disposal apparatus of claim 6, further comprising:

auxiliary power supply means for supplying power to said electrode moving means in the injection needle safety disposal apparatus.

8. An injection needle safety disposal apparatus of claim 1, further, comprising:

deodorizing means for deodorizing air exposed thereto; and exhaust means for discharging the air in the vicinity of said electrodes after it has been led to said deodorizing means and deodorized, said exhaust means being a positive-displacement type pump.

9. An injection needle safety disposal apparatus of claim 8, further comprising:

auxiliary power supply means for supplying power to said electrode moving means in the injection needle safety disposal apparatus.

10. An injection needle safety disposal apparatus of claim 1 further comprising:

auxiliary power supply means for supplying power to said roller-rotation driving means in the injection needle safety disposal apparatus.

11. A apparatus for disposal of an instrument including a metallic needle portion, the apparatus comprising;

a pair of electrodes symmetric about, and having a circular cross-section with respect to, corresponding axes of rotation thereof, said axes of rotation being sufficiently spaced apart from one another to create a gap between said pair of electrodes, said pair of electrodes oriented such that both of said pair of electrodes are simultaneously contactable by said needle portion when said needle portion is positioned crosswise said axes of rotation of said pair of electrodes;

means for rotating each of said pair of electrodes about a corresponding one of said axes of rotation;

means for applying an electrical potential between said pair of electrodes; and means for positioning and maintaining said needle portion crosswise said axes of rotation and in simultaneous contact engagement with both of said pair of electrodes to initiate current flow therebetween through said needle portion to produce heat sufficient to disintegrate a portion of said needle portion extending between points of contact with said pair of electrodes.

12. The apparatus of claim 11, wherein:

said means for applying an electrical potential between said pair of electrodes include a cam-shaped ring carried on and conductive with each of said pair of electrodes and rotatable therewith; and said means for applying an electrical potential further includes a brush contactable with each said cam-shaped ring, each said cam-shaped ring including discontinuous surface configuration for intermittently contacting and at least partially breaking contact with said brush as said cam-shaped ring rotates.

13. The apparatus of claim 11, further comprising:

a scraper provided near at least one of said pair of electrodes, said scraper and said at least one of said pair of electrodes counter-rotate.

14. The apparatus of claim 11, wherein:

said means for positioning orients said needle portion to extend through said gap and passing between said pair of electrodes, to effect contact with both of said pair of electrodes on opposite facing sides thereof.

15. The apparatus of claim 14, wherein:

said pair of electrodes counter-rotate.

16. The apparatus of claim 15, wherein:

said pair of electrodes are rotated on corresponding directions such that said needle portion is drawn in a direction of insertion between said pair of electrodes.

17. The apparatus of claim 14, further comprising:

means for selectively altering a width of said gap between which said needle portion extends, for accommodation of needle portions of different diameters.

18. The apparatus of claim 17, wherein:

each of said pair of electrodes is elongated in the direction of a corresponding one of said axes of rotation, said axes of rotation being approximately parallel with one another; and said means for selectively altering a width of said gap includes a configuration of at least one of said pair of electrodes presenting a longitudinally tapered shape, whereby said gap varies continuously as a function of longitudinal position.

19. The apparatus of claim 17, wherein:

each of said pair of electrodes is elongated in the direction of a corresponding one of said axes of rotation, said axes of rotation being codirectional; and said means for selectively altering a width of said gap includes a configuration of one of said pair of electrodes presenting a series of steps arranged in the longitudinal direction, whereby said gap varies incrementally as a function of longitudinal position.

20. The apparatus of claim 17, wherein:

each of said pair of electrodes is elongated in the direction of a corresponding one of said axes of rotation; and said means for selectively altering a width of said gap includes divergently positioning said axes of rotation, whereby said gap varies as a function of longitudinal position.

21. The apparatus of claim 19, wherein:

said means for selectively altering a width of said gap includes movably biasing a one of said electrodes towards a remaining one of said electrodes.

* * * * *